United States Patent [19]

Poe et al.

[11] 4,258,045
[45] Mar. 24, 1981

[54] INHIBITOR OF DIHYDROFOLATE REDUCTASE

[75] Inventors: Martin Poe; William V. Ruyle, both of Scotch Plains, N.J.

[73] Assignee: Merck & Co., Inc., Rahway, N.J.

[21] Appl. No.: 99,167

[22] Filed: Nov. 30, 1979

[51] Int. Cl.³ ............... A61K 31/505; C07D 239/49; C07D 239/49
[52] U.S. Cl. ................ 424/251; 260/239.75; 260/465 E; 544/325
[58] Field of Search ............ 424/251; 544/325; 260/239.75

[56] References Cited

U.S. PATENT DOCUMENTS

| | | | |
|---|---|---|---|
| 2,909,522 | 10/1959 | Hitchings et al. | 544/325 |
| 3,049,544 | 8/1962 | Stenbuck et al. | 544/325 |
| 3,692,787 | 9/1972 | Roth et al. | 424/251 X |
| 3,931,181 | 1/1976 | Kompis et al. | 424/251 X |
| 3,992,379 | 11/1976 | Liebenow et al. | 544/325 |

OTHER PUBLICATIONS

Lednicer et al., The Organic Chemistry of Drug Synthesis, pp. 120 to 123, John Wiley & Sons, NY, (1977).

Primary Examiner—John D. Randolph
Attorney, Agent, or Firm—William H. Nicholson; Mario A. Monaco

[57] ABSTRACT

A group of aryl-Z-alkoxy-5-benzylpyrimidines wherein Z is oxy, thio, imino, carbonyl, carbamoyl, sulfonyl, sulfinyl or sulfamoyl has been prepared from 2,4-diamino-5-benzylpyrimidine via alkylation with either an aryl-Z-alkyl halide or a substituted glycidyl ether. These compounds are potent dihydrofolate reductase (DHFR) inhibitors which are useful as antibacterial, anti-protozoal and antitumor agents.

6 Claims, No Drawings

INHIBITOR OF DIHYDROFOLATE REDUCTASE

BACKGROUND

The present invention relates to novel aryl-Z-alkoxy-5-benzylpyrimidines wherein Z is oxy, thio, imino, carbonyl, carbamoyl, sulfonyl, sulfinyl or sulfamoyl.

These compounds are potent inhibitors of dihydrofolate reductase (DHFR) which catalyzes the reduction of dihydrofolic acid to tetrahydrofolic acid (THFA), a widely used one-carbon carrier of metabolism. As a result, the novel compounds of this invention behave as folate antogonists and inhibit the growth of microorganisms by interfering with their reduction of dihydrofolic acid.

Conventionally, effective inhibition of microorganism growth has been achieved by the combined action of a benzyldiaminopyrimidine DHFR inhibitor such as trimethoprim (U.S. Pat. No. 3,049,544) and a sulfa drug including various derivatives of sulfanilamide which is thought to prevent dihydrofolate biosynthesis, (D. Lednicer and L. A. Mitscher, The Organic Chemistry of Drug Synthesis, John Wiley and Sons, New York, pp. 120–123, 1977). The combination of benzyldiaminopyrimidine and sulfa drug may exert their synergistic action through their ability to simultaneously inhibit DHFR. However, the combination therapy suffers from (1) allergic reactions due to sulfa drugs; and (2) problem of differing rates of metabolism and clearance of the components.

Accordingly it is an object of the present invention to provide novel phenyl-Z-alkoxy-5-benzylpyrimidines which encompass within one molecule a benzylpyrimidine moiety to block the MTX (methotrexate) site of DHFR; and an aryl-Z-alkoxy structure to block the adjacent "sulfa" site as well. The resulting "intramolecular" synergestic action is superior to that achieved by the combination therapy involving a benzylpyrimidine and a sulfa drug.

It is also an object of this invention to provide a new process for preparing the novel compounds of this invention.

A further object of this invention is to provide a novel method or utilizing these novel compounds as folate antagonists having antibacterial, anti-protozoal, and antitumor activities.

Still another object of this invention is to provide novel pharmaceutical compositions comprising one or more of the novel compounds of this invention as active ingredients.

DETAILED DESCRIPTION OF THE INVENTION

The present invention concerns novel aryl-Z-alkoxy-5-benzylpyrimidines of the structural formula:

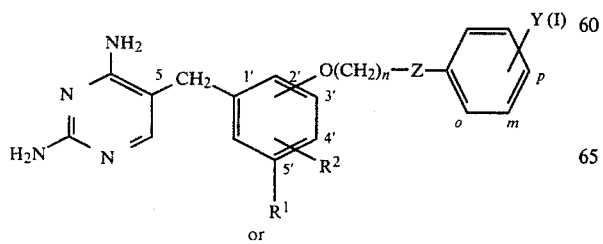

or

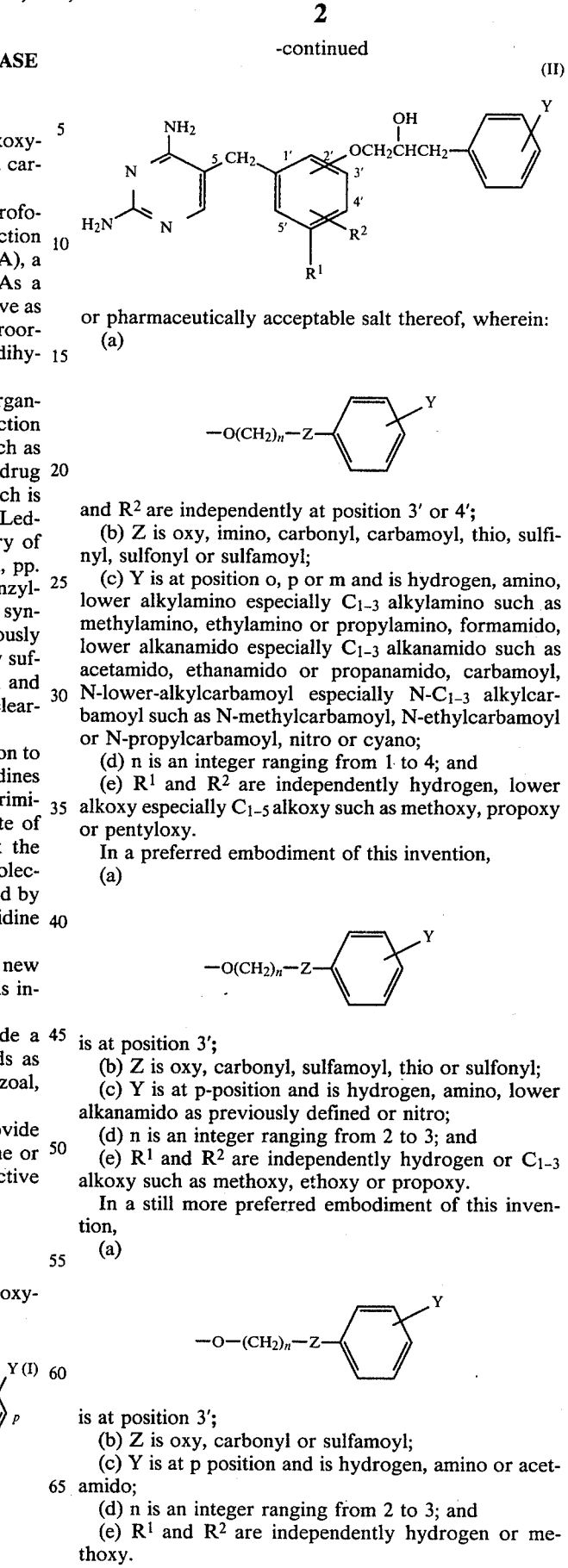

or pharmaceutically acceptable salt thereof, wherein:

(a)

$$-O(CH_2)_n-Z-\bigcirc-Y$$

and $R^2$ are independently at position 3' or 4';

(b) Z is oxy, imino, carbonyl, carbamoyl, thio, sulfinyl, sulfonyl or sulfamoyl;

(c) Y is at position o, p or m and is hydrogen, amino, lower alkylamino especially $C_{1-3}$ alkylamino such as methylamino, ethylamino or propylamino, formamido, lower alkanamido especially $C_{1-3}$ alkanamido such as acetamido, ethanamido or propanamido, carbamoyl, N-lower-alkylcarbamoyl especially N-$C_{1-3}$ alkylcarbamoyl such as N-methylcarbamoyl, N-ethylcarbamoyl or N-propylcarbamoyl, nitro or cyano;

(d) n is an integer ranging from 1 to 4; and (e) $R^1$ and $R^2$ are independently hydrogen, lower alkoxy especially $C_{1-5}$ alkoxy such as methoxy, propoxy or pentyloxy.

In a preferred embodiment of this invention, (a)

$$-O(CH_2)_n-Z-\bigcirc-Y$$

is at position 3';

(b) Z is oxy, carbonyl, sulfamoyl, thio or sulfonyl;

(c) Y is at p-position and is hydrogen, amino, lower alkanamido as previously defined or nitro;

(d) n is an integer ranging from 2 to 3; and (e) $R^1$ and $R^2$ are independently hydrogen or $C_{1-3}$ alkoxy such as methoxy, ethoxy or propoxy.

In a still more preferred embodiment of this invention, (a)

$$-O-(CH_2)_n-Z-\bigcirc-Y$$

is at position 3';

(b) Z is oxy, carbonyl or sulfamoyl;

(c) Y is at p position and is hydrogen, amino or acetamido;

(d) n is an integer ranging from 2 to 3; and (e) $R^1$ and $R^2$ are independently hydrogen or methoxy.

Finally, the most preferred embodiment of this invention includes the following compounds:

2,4-diamino-5-{3'-[2''-(p-sulfanilamido)ethoxy]-4'-methoxybenzyl}pyrimidine 2,4-diamino-5-{3'-[3''-(p-sulfanilamido)propoxy]-4'-methoxybenzyl}pyrimidine 2,4-diamino-5-[3'-(3''-benzoylpropoxy)-4'-methoxybenzyl]pyrimidine 2,4-diamino-5-[3'-(2''-phenoxyethoxy)-4'-methoxybenzyl]pyrimidine.

As the novel compounds of this invention are organic bases, their pharmaceutically acceptable salts are those resulting from the neutralization of the base with an acid. The acid employed is usually an inorganic acid such as a hydrohalic acid such as hydrochloric or hydrobromic acid; sulfuric acid; nitric acid; or phosphoric acid. An organic acid such as maleic, fumaric, tartaric, citric, acetic, salicylic, succinic, benzoic, benzenesulfonic, glutamic, lactic or isethionic acid is also commonly used. Generally the neutralization is conducted in an inert solvent such as water; a $C_{1-3}$ alkanol such as methanol, ethanol or isopropanol; a $C_{3-6}$-ketone such as acetone, or ethylmethyl ketone; an etheral solvent such as diethyl ether, tetrahydrofuran or dioxane; acetonitrile; or an aromatic solvent such as toluene. Mixtures of the above described solvents are also employed. Generally the neutralization is carried out in aqueous ethanol, at 0°–75° C., preferably at 0°–25° C., followed by filtration to collect the salts.

The novel compounds of structure (I) of this invention are prepared by a process comprising treating an appropriately substituted 2,4-diamino-5-benzylpyrimidine with an alkylating reagent in the presence of a base as described below.

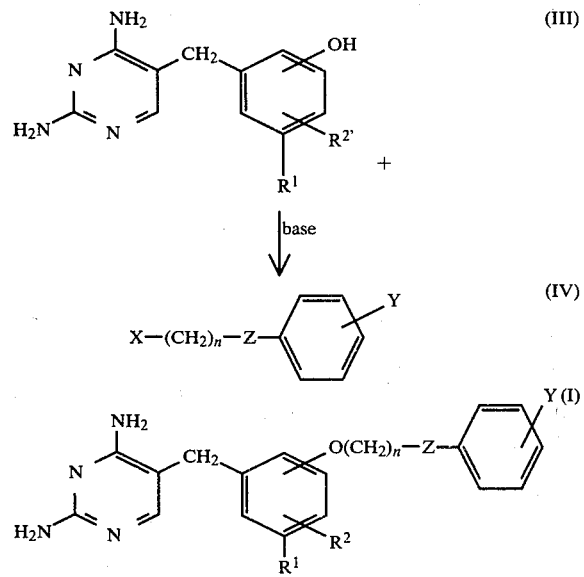

wherein the relative positions of —OH, $R^2$ and

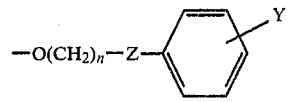

as well as the definitions of $R^1$ $R^2$, Y, and Z are as previously defined; and X is halo such as chloro, bromo, or iodo.

The reaction is generally carried out in an inert solvent such as a $C_{1-4}$ alkanol, for example methanol, ethanol, n-propanol, or t-butanol; a fluoro-$C_{1-4}$ alkanol such as 2,2,2-trifluoroethanol or perfluorobutanol; a chloro $C_{1-4}$ alkane such as chloroform, methylene chloride or 1,2-dichloroethane; or an ether such as diethylether, tetrahydrofuran, dioxane, or 1,2-dimethoxyethane; water; or a mixture thereof. The preferred solvent system being aqueous alkanol solutions.

Inorganic strong bases such as sodium hydroxide, lithium hydroxide, potassium hydroxide, calcium hydroxide, sodium or potassium carbonate are often used to facilitate the reaction. Occasionally organic bases such as pyridine, or a trialkylamine, for example, triethylamine, or tributylamine can also be used. Sodium hydroxide and potassium hydroxide are the preferred bases for this reaction.

Usually the reaction mixture is maintained at about 10°–120° C. preferably at about 60°–100° C. until reaction is substantially complete which requires about 30 min. to about 48 hours. Under the preferred conditions, i.e., in aqueous $C_{1-4}$ alkanol at about 60°–100° C., the reaction is essentially over within about 20 hr.

The novel compounds of formula (II) are prepared by a process comprising treating the benzylpyrimidine (III) with a substituted glycidyl ether of formula:

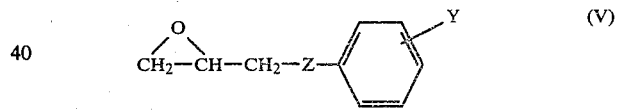

wherein Y and Z are as previously defined. The process is carried out in substantially the same manner as described above for the preparation of compounds of formula (I).

The starting materials used in the processes for the preparation of compounds (I) and (II) can be prepared, insofar as they are not known or described in the Examples, according to the following scheme, in analogy to the procedures disclosed in U.S. Pat. No. 3,049,544.

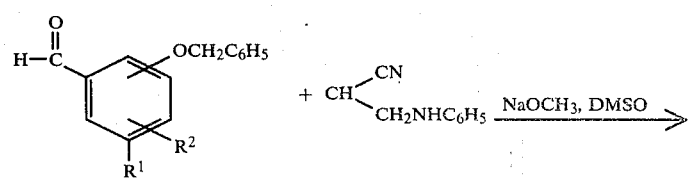

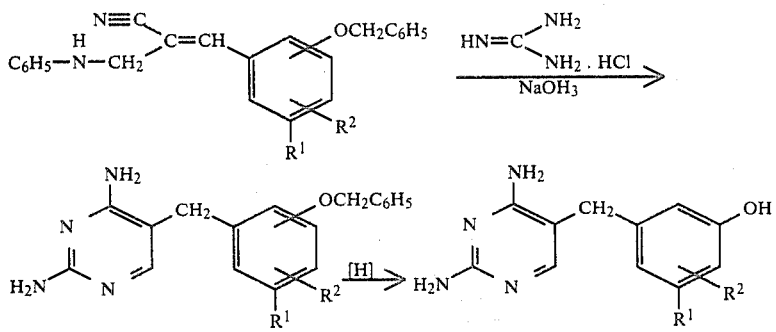

The compounds of formula (I) and (II) and their pharmaceutically acceptable salts are active as antibacterial, antiprotozoal and antitumor agents. They are also useful in the study of transport properties of dihydrofolate reductase inhibitors. To incorporate such activities in a novel method of treatment for bacterial infections, protozoal diseases and cancer, one or more of the compounds of formula (I) and (II) can be administered to a mammalian species including humans, orally, rectally and parenterally, for example, by incorporating a therapeutic dosage (from about 0.05 to about 200 mg per kg of body weight, preferably from about 0.5 to about 10 mg per kg of body weight in a single dose or in 2 to 4 divided doses), in a conventional dosage form, such as tablets, capsules, elixirs, suspensions, solutions or the like, preferably tablets. They can be administered to a patient in mixture with convention pharmaceutical carriers or excipients, such as corn starch, calcium stearate, magnesium carbonate, calcium silicate, dicalcium phosphate, talc, lactose, or the like. Moreover, they can be administered in the presence of buffers, or agents used to adjust to isotonicity, and the pharmaceutical dosage form can, if desired, be subject to conventional pharmaceutical expedients such as sterilization. The amount of an active compound in such a therapeutically useful compositon or preparation usually ranges from 1 to 500 mg preferably 5-250 mg, per unit dosage.

The following examples further illustrate the invention.

EXAMPLE 1

2,4-Diamino-5-{3'-[2''-(N$^4$-acetylsulfanilamido)ethoxy]-4'-methoxybenzyl}pyrimidine

Step A: Preparation of 3-Benzyloxy-4-methoxy-β-cyano-N-phenylcinnamylamine

To a mixture of 88 g (0.364 mole) of 3-benzyloxy-4-methoxybenzaldehyde, 67.5 g of 3-anilinopropionitrile and 90 ml of dimethylsulfoxide which has been heated to 95° is added a slurry of 3.1 g of sodium methoxide in 60 ml of dimethyl sulfoxide with stirring. The temperature is then raised to 125°–130° for 2 hr. After cooling, the mixture is poured into 1600 ml of ice-water with stirring. The precipitated product is collected and triturated with cold ethanol and with ether to give 75 g (55.6%). This intermediate is used without further purification in the following step.

Step B: Preparation of 2,4-Diamino-5-(3-benzyloxy-4-methoxybenzyl)pyrimidine 75 Grams (0.5 mole) of crude 3-benzyloxy-4-methoxy-β-cyano-N-phenylcinnamylamine is added to a suspension made by stirring 40 g (0.42 mole) of guanidine hydrochloride with 27.5 g (0.51 mole) of sodium methoxide in 320 ml of ethanol. The reaction mixture is stirred and heated at reflux for 1.5 hr., after which the mixture becomes quite thick. An additional 320 ml of ethanol is added, and the refluxing is continued for a total of 20 hr. Most of the ethanol is removed by vacuum distillation, the resulting residue is stirred with 1500 ml of water and washed well with water. The crude moist product is digested with 250 ml of hot ethanol, cooled, filtered, and washed with ethanol and with water to yield 55 g (81%) of 2,4-diamino-5-(3-benzyloxy-4-methoxybenzyl)pyrimidine, m.p. 210°–212°.

Step C: Preparation of 2,4-Diamino-5-(3'-hydroxy-4'-methoxybenzyl)pyrimidine hydrochloride A solution of 55 g (0.15 mole) of 2,4-diamino-5-(3-benzyloxy-4-methoxybenzyl)pyrimidine from the preceding step in 2500 ml of methanol and 20 ml of concentrated hydrochloric acid is hydrogenated at about 2.5 to 3.0 atm. in the presence of 4 g of 10% Palladium-on-charcoal catalyst. After the uptake of hydrogen has stopped (3.5 hr.) the catalyst is filtered and the filtrate concentrated in vacuo to 250 ml. The crystalline product weighs 41.5 g (90%), m.p. 230°–32°.

Step D: Preparation of N$^1$-(2-bromoethyl)-N$^4$-acetylsulfanilamide

A suspension of 30.7 g (0.15 mole) of 2-bromoethylamine hydrobromide and 23.4 g (0.10 mole) of N-acetylsulfanilyl chloride in 200 ml of water is stirred in a 1 liter beaker while 21.2 g (0.2 mole) of sodium carbonate is added in portions. After 2 hours, the reaction product is filtered, washed with water, dried in vacuo at 60°, and recrystallized from methylethyl ketone to yield 10.2 g, of purified product, m.p. 165°–167°.

Employing substantially the same procedure as described in Example 1, Step D, but substituting for 2-bromoethylamine used therein 3-bromopropylamine hydrobromide, there is produced N$^1$-(3-bromopropyl)-N$^4$-acetylsulfanilamide.

Step E: Preparation of 2,4-Diamino-5-{3'-[2''-(N$^4$-acetylsulfanilamido)ethoxy]-4'-methoxybenzyl}pyrimidine A mixture of 1.41 g (0.005 mole) of 2,4-diamino-5-(3'-hydroxy-4'-methoxybenzyl)pyrimidine hydrochloride, 2.0 g (0.00625 mole) of N$^1$-(2-bromoethyl)-N$^4$-acetylsulfanilamide, 25 ml of methanol, and 6.0 ml of an aqueous solution containing 0.013 mole of potassium hydroxide is heated at reflux for 1.5 hr.

After cooling, a small amount of insoluble material is filtered off. The filtrate is concentrated by vacuum distillation and diluted with water to precipitate the oily crude product. The latter is fractionally crystallized or chromatographed on silica gel to obtain the pure produce. Yield 30–40%, m.p. 131°–134° dec. Recrystallization from aqueous ethanol does not change the melting point. Thin layer chromatography on silica gel, with 8.2 (v/v) chloroform-methanol elution, shows a single spot, $R_f$ 0.6.

Proton magnetic resonance, infrared, and mass spectra are all in accord with the assigned structure.

Elemental analysis indicates that the compound crystallizes as the monohydrate of 2,4-diamino-5-{3'-[2''-(N$^4$-acetylsulfanilamido)ethoxy]-4'-methoxybenzyl}-pyrimidine. Anal. Calcd for $C_{22}H_{26}N_6O_5S \cdot H_2O$: C, 52.37; H, 5.59; N, 16.66. Found: C, 51.96; H, 5.66; N, 16.25.

Employing the procedure substantially as described in Example 1, Step E, but substituting for N$^1$-(2-bromoethyl)-N$^4$-acetylsulfanilamide used therein an equimolar amount of one of the following alkylating reagents:
(1) N$^1$-(4-bromobutyl)-N$^4$-acetylsulfanilamide
(2) N$^1$-(2-bromoethyl)-p-nitrobenzenesulfonamide
(3) N$^1$-(2-bromoethyl)benzenesulfonamide
(4) N$^1$-(3-chloropropyl)-N$^4$-acetylsulfanilamide
(5) 3-phenoxypropyl bromide
(6) 3-(p-nitrophenoxy)propyl bromide
(7) 2-phenoxyethyl bromide
(8) 4-phenoxybutyl bromide
there are produced the corresponding alkylated 2,4-diamino-5-(3'hydroxy-4'-methoxybenzyl)pyrimidines as follows:
(1) 2,4-Diamino-5-{3'-[4''-(N$^4$-acetylsulfonamido)-butoxy]-4'-methoxybenzyl}pyrimidine
(2) 2,4-Diamino-5-{3'-[2''-(p-nitrobenzenesulfonamido)ethoxy]-4'-methoxybenzyl}pyrimidine
(3) 2,4-Diamino-5-[3'-(2''-benzenesulfonamidoethoxy)-4'-methoxybenzyl]]pyrimidine
(4) 2,4-Diamino-5-{3'-[3''-(N$^4$-acetylsulfanilamido)-propoxy]-4-methoxybenzyl}pyrimidine
(5) 2,4-Diamino-5-[3'-(3''-phenoxypropoxy)-4'-methoxybenzyl]pyrimidine
(6) 2,4-Diamino-5-{3'-[3''-(p-nitro-phenoxy)propoxy]-4methoxybenzyl}pyrimidine
(7) 2,4-Diamino-5-[3'-(2''-phenoxyethoxy)-4'-methoxybenzyl]pyrimidine
(8) 2,4-Diamino-5-[3'-(4''-phenoxybutoxy)-4'-methoxybenzyl]pyrimidine.

Employing the procedure substantially as described in Example 1, Step E, but substituting for 2,4-diamino-5-(3'-hydroxy-4'-methoxybenzyl)pyrimidine hydrochloride used therein, an equimolar amount of the corresponding 4'5'-dimethoxy analog there is prepared 2,4-diamino-5-3'[2''-(p-sulfanilamido)ethoxy]-4'5'-dimethoxybenzyl pyrimidine.

EXAMPLE 2

2,4-Diamino-5-[3'-methoxy-4'-(3''-phenoxypropoxy)benzyl]pyrimidine

Step A: Preparation of 2,4-Diamino-5-(3'-methoxy-4'-hydroxybenzyl)pyrimidine hydrochloride In a manner substantially analogous to that described in Example 1, Steps A–C, but substituting for 3-benzyloxy-4-methoxybenzaldehyde used therein, an equimolar amount of 3-methoxy-4-benzyloxybenzaldehyde, there is prepared 2,4-diamino-5-(3'-methoxy-4'-hydroxybenzyl)pyrimidine hydrochloride.

Step B: Preparation of 2,4-Diamino-5-[3'-methoxy-4'-(3''-phenoxypropoxy)-benzyl]pyrimidine A mixture of 1.42 g of 2,4-diamino-5-(3'-methoxy-4'-hydroxybenzyl)pyrimidine hydrochloride, 1.2 g of 3-phenoxypropyl bromide, 30 ml of methanol and 5 ml of an aqueous solution containing 0.6 g of potassium hydroxide is heated at reflux for 1.5 hr. A total of 1.66 g of product is obtained by diluting the reaction mixture with water. The crude product is heated with 50 ml ethanol, filtered, and the filtrate is treated with 25 ml of water. Substantially pure product crystallizes. A final crystallization from methylene chloride-hexane provides pure 2,4-Diamino-5-[3'-methoxy-4'-(3''-phenoxypropoxy)benzyl]-pyrimidine. Anal. Calcd for $C_{21}H_{24}N_4O_3$: C, 66.30, H, 6.36; N, 14.73. Found: C, 66.25; H, 6.34; N, 14.48.

Employing the procedure substantially as described in Example 2, Step B, but substituting for 3-phenoxypropylbromide used therein an equimolar amount of one of the following alkylating agents:
(1) N$^1$-(2-bromoethyl)-N$^4$-acetylsulfanilamide
(2) N$^1$-(3-bromopropyl)-N$^4$-acetylsulfanilamide
(3) 2-phenoxyethyl bromide
(4) 3-phenoxypropyl bromide
(5) 4-phenoxybutyl bromide
(6) 3-(p-nitrophenoxy)propyl bromide
(7) N$^1$-(2-bromoethyl)benzene-sulfonamide
(8) N$^1$-(2-bromomethyl)-p-nitro-benzenesulfonamide
there are produced the following corresponding 4-substituted derivatives of 2,4-diamino-5-(4'-hydroxy-3'-methoxybenzyl)pyrimidines:
(1) 2,4-diamino-5-{4'-[2''-(N$^4$-acetylsulfanilamido)ethoxy]-3'-methoxybenzyl}pyrimidine
(2) 2,4-diamino-5-{4'-[3''-(N$^4$-acetylsulfanilamido)-propoxy]-3'-methoxybenzyl}pyrimidine
(3) 2,4-Diamino-5-[3'-methoxy-4'-(2''-phenoxyethoxy)-benzyl]pyrimidine
(4) 2,4-Diamino-5-[3'-methoxy-4'-(3''-phenoxypropoxy)-benzyl]pyrimidine
(5) 2,4-Diamino-5-[3'-methoxy-4'-(4''-phenoxybutoxy)-benzyl]pyrimidine
(6) 2,4-diamino-5-{3'-methoxy-4'-[3''-(p-nitrophenoxypropoxy]benzyl}pyrimidine
(7) 2,4-diamino-5-[4'-(2''-benzenesulfonamidoethoxy)-3'-methoxybenzyl]pyrimidine
(8) 2,4-diamino-5-{4'-(3''-p-nitro-benzensulfonamido)ethoxy]-3'-methoxybenzyl}pyrimidine.

EXAMPLE 3

2,4-Diamino-5-{3'-[3''-(N$^4$-acetylsulfanilamido)propoxy]-4'-methoxybenzyl}pyrimidine A mixture of 2.82 g (0.01 mole) of 2,4-diamino-5-(3'-hydroxy-4'-methoxybenzyl)pyrimidine hydrochloride, 3.36 g (0.01 mole) of N$^1$-(3-bromopropyl)-N$^4$-acetylsulfanilamide, 2.76 g of anhydrous $K_2CO_3$, and 20 ml of dimethylformamide is heated with stirring at 100° for 18 hr. The mixture is concentrated in vacuo to a dark oil, which is shaken with a mixture of water and chloroform. The oily material which remaines insoluble in the water and chloroform is chromatographed on silica gel. Elution with chloroform-methanol, (85:15) gives fractions containing 0.55 g (11%) of 2,4-diamino-5-{3'-[3''-(N$^4$-acetylsulfanilamido)propoxy-4'-methoxybenzyl}- pyrimidine, m.p. 96°–98°. Spectral data are consistent with the proposed structure.

Anal. Calcd for $C_{23}H_{28}N_6O_5S$: C, 55.19; H, 5.64; N, 16.70. Found: C, 57.73; H, 5.62; N, 16.21.

EXAMPLE 4

2,4-Diamino-5{3′-[2′′-(p-sulfanilamido)ethoxy]-4′-methoxybenzyl}pyrimidine 2,4-Diamino-5-{3′[2′′-(N⁴-acetylsulfanilamido)ethoxy]-4′-methoxybenzyl}pyrimidine monohydrate, 100 mg, is heated at 95° with 1 ml of 6 N HCl for 1 hr. After cooling, the resulting crystals are collected and washed with cold ethanol and with ether. Yield 70 mg (66%), m.p. 225°–227° dec.

Proton magnetic resonance, infrared, and mass spectra are in accord with the assigned structure.

Elemental analysis indicates that the product is the bis-hydrochloride of the title compound.

Anal. Calcd for $C_{20}H_{24}N_6O_4S.2HCl$: C, 46.42; H, 5.06; N, 16.24; Cl, 13.70. Found: C, 45.80; H, 5.06; N, 15.72; Cl, 13.76.

A hot solution of the bis-hydrochloride is treated with an excess of ammonium hydroxide to give 2,4-diamino-5-{3′-[2′′-(p-sulfanilamido)ethoxy]-4′-methoxybenzyl}pyrimidine, m.p. 207°–208°.

Employing the procedure substantially as described above, but substituting for 2,4-diamino-5-{3′-[2′′-(N⁴-acetylsulfanilamido)ethoxy]-4′-methoxybenzyl}pyrimidine used therein, an equimolar amount of one of the following compounds:

(1)  2,4-Diamino-5-{3′-[3′′-(N⁴-acetylsulfanilamido)propoxy]-4′-methoxybenzyl}pyrimidine
(2)  2,4-Diamino-5-{3′-[2′′-(N⁴-acetylsulfanilamido)ethoxy]-4′,5′-dimeethoxybenzly}pyrimidine
(3)  2,4-Diamino-5-{4′-[2′′-(N⁴-acetylsulfanilamido)ethoxy]-3′-methoxybenzyl}pyrimidine
(4)  2,4-Diamino-5-{4′-[3′′-(N⁴-acetylsulfanilamido)propoxy]-3′-methoxybenzyl}pyrimidine.

There are produced respectively, (1)  2,4-Diamino-5-{3′-(p-sulfanilamido)propoxy-4′-methoxybenzyl}pyramidine, m.p. 194°–196°.

Anal. Calc'd for $C_{21}H_{26}N_6O_4S.H_2O$: C, 52.93; H, 5.92; N, 17.94. Found: C, 52.73; H, 5.95; N, 16.95.

(2)  2,4-Diamino-5-{3′-[2′′-(p-sulfanilamido)ethoxy]-4′,5′-dimethoxybenzyl}pyrimidine.
(3)  2,4-Diamino-5-{4′-[2′′-(p-sulfanilamido)ethoxy]-3′-methoxybenzyl}pyrimidine.
(4)  2,4-Diamino-5-{4′-[3′′-(p-sulfanilamido)propoxy]-3′-methoxybenzyl}pyrimidine.

EXAMPLE 5

2,4-Diamino-5-{3′-[3′′-(p-acetamidophenylthio)propoxy]-4′-methoxybenzyl}pyrimidine Step A: Preparation of 3-(p-acetamidophenylthio)propanol A mixture of 16.7 g (0.1 mole) of p-mercaptoacetanilide, 4 g of sodium hydroxide, 40 ml of water, 40 ml of 1,2-dimethoxyethane, and 0.39 g (0.11 mole) of 3-chloropropanol is heated in a steam bath with stirring for 30 minutes. Two liquid phases are formed, and TLC indicates that the reaction is substantially complete. The mixture is distilled in vacuo to remove 1,2-dimethoxyethane, and the oily mixture which separates is triturated with cold water until it solidifies. The crude product is recrystallized from ethanol to obtain a by-product: the disulfide derived from the starting mercapto compound. The ethanol filtrate is concentrated, and the residue is triturated with ether-hexane to obtain 15.7 g of the desired product. Recrystallization from ethyl acetate-hexane gives 11.8 g of 3-(p-acetamidophenylthio)propanol which shows the correct IR and NMR spectra.

Step B: Preparation of 3-(p-acetamidophenylthio)propyl chloride

To a stirred suspension of 5.62 g (0.025 mole) of 3-(4′-acetamidophenylthio)propanol in 25 ml of methylene chloride and 2.03 ml of pyridine (0.025 mole) is added 3.7 g of thionyl chloride (0.031 mole) in 10 ml of methylene chloride. After the exothermic reaction subsides, the mixture is heated at reflux for 0.5 hr. The reaction mixture is poured into 100 ml of ice-water with stirring. The organic layer is separated, dried and concentrated to a dark red solid. Extraction of the latter with ether in a Soxlet apparatus yields 3.5 g of 3-(p-acetamidophenylthio)propyl chloride having the correct IR and NMR spectra.

Step C: Preparation of 2,4-Diamino-5-{3′-[3′′-(p-acetamidophenylthio)propoxy]-4-methoxybenzyl}pyrimidine A mixture of 3.6 g of 2,4-diamino-5-(3′-hydroxy-4′-methoxybenzyl)pyrimidine hydrochloride, 3.4 g of 3-(p-acetamidophenylthio)propyl chloride, 3.8 ml of methanol, 12 ml of an aqueous solution containing 0.027 mole of potassium hydroxide and 0.2 g of potassium iodide is heated at reflux for 20 hr. The mixture is cooled and filtered to remove a small amount of inorganic material. Water, (75 ml) is added to the filtrate, and the methanol is removed by vacuum distillation. After the addition of 50 ml of methylene chloride the mixture is stirred for 30 min. and then filtered to obtain a crystalline product. After twice recrystallizing from 50% aqueous ethanol the product 2,4-diamino-5-{3′-[3′′-(p-acetamidophenylthio)propoxy]-4′-methoxybenzyl}pyrimidine, weighes 1.94 g and has m.p. 175°–177°.

Employing essentially the procedure as described in Example 5, Step C, but substituting for the 3-(p-acetamidophenylthio)propyl chloride used therein, an equimolar amount of 2-(p-acetaminophenylthio)ethylchloride, there is produced 2,4-diamino-5-{3′-[2′′-(p′-acetamidophenylthio)ethoxy]-4′-methoxybenzyl}-pyrimidine.

EXAMPLE 6

2,4-Diamino-5-[3′-(2′′-hydroxy-3′′-phenoxy)propoxy-4′-methoxybenzyl]pyrimidine

A mixture of 1.41 g (0.005 mole) of 2,4-diamino-5-(3′-hydroxy-4′-methoxybenzyl)pyrimidine hydrochloride, 0.75 g of phenyl glycidyl ether (0.005 mole), 25 ml. of ethanol, and 2.8 ml of an aqueous solution containing 0.006 mole of potassium hydroxide is heated at reflux for 2.5 hr. Another portion of 0.75 g of phenyl glycidyl ether is added and reflux is continued for 4.75 hr. The mixture is cooled, some inorganic material is removed by filtration, and the filtrate is concentrated and chromatographed on silica gel. Elution with chloroform-methanol (10:1 v/v) furnishes 0.64 g of 2,4-Diamino-5-[3′-(2′′-hydroxy-3′′-phenoxy)propoxy-4′-methoxybenzyl]pyrimidine. TLC indicates homogeneity. Anal. Calcd for $C_{21}H_{24}N_4O_4$: C, 63.62; H, 6.10; N, 14.13 Found: C, 63.32; H, 6.14; N, 13.62.

Following substantially the same procedure as described above, but substituting for the phenyl glycidyl ether used therein an equimolar amount of (1) p-nitro- or (2) p-acetamido-phenyl glycidyl either, there are produced respectively, (1) 2,4-Diamino-5-{3'-[2''-hydroxy-3''-(p-nitrophenoxy)propoxy]-4'-methoxybenzyl}pyrimidine Anal. Calcd for $C_{21}H_{23}N_5O_6.\frac{1}{2} H_2O$: C, 56.00; H, 5.37; N, 15.54. Found C, 56.44; H, 5.19; N, 15.35.

(2) 2,4-Diamino-5-{3'-[2''-hydroxy-3''-(p-acetamidophenoxy)propoxy]-4'-methoxybenzyl}pyrimidine Employing the procedure substantially as described above, using p-nitro-phenylglycidyl ether, but substituting for 2,4-diamino-5-(3'-hydroxy-4'-methoxybenzyl)pyrimidine used therein an equimolar amount of one of the following substituted pyrimidines.

(1) 2,4-Diamino-5-(4'-hydroxy-3'-methoxybenzyl)pyrimidine
(2) 2,4-diamino-5-(4'-hydroxy-3'-ethoxybenzyl)pyrimidine
(3) 2,4-Diamino-5-(3'-hydroxy-4'-propoxybenzyl)pyrimidine
(4) 2,4-Diamino-5-(3'-hydroxy-4',5'-dimethoxybenzyl)pyrimidine
(5) 2,5-Diamino-5-(4'-hydroxy-3',5'-dimethoxybenzyl)pyrimidine
(6) 2,4-Diamino-5-(3'-hydroxy-4'-ethoxy-5'-methoxybenzyl)pyrimidine there are produced the corresponding propoxybenzylpyrimidines (1) 2,4-Diamino-5-{4'-[2''-hydroxy-3''-(p-nitrophenoxy)propoxy]-3'-methoxybenzyl}pyrimidine
(2) 2,4-Diamino-5-}4'-[2''-hydroxy-3''-(p-nitrophenoxy)propoxy]-3'-ethoxybenzyl}pyrimidine
(3) 2,4-Diamino-5-{3'-[2''-hydroxy-3''p-nitrophenoxy)propoxy]-4'-propoxybenzyl}pyrimidine
(4) 2,4-Diamino-5-{3'-[2''-hydroxy-3''-(p-nitrophenoxy)propoxy]-4',5'-dimethoxybenzyl}pyrimidine
(5) 2,4-Diamino-5-{4'-[2''-hydroxy-3''-(p-nitrophenoxy)propoxy]-3',5'-dimethoxybenzyl}pyrimidine
(6) 2,4-Diamino-5-{3'-[2''-hydroxy-3''-(p-nitrophenoxy)propoxy]-4'-ethoxy-5'-methoxybenzyl}pyrimidine.

EXAMPLE 7

2,4-Diamino-5-{3'-[2''-hydroxy-3''-(p-aminophenoxy)propoxy]-4'-methoxybenzyl}pyrimidine bishydrochloride monohydrate 2,4-Diamino-5-{3'-[2''-hydroxy-3''-(p-nitrophenoxy)propoxy]-4'''-methoxybenzyl{pyrimidine is treated with hydrogen under the catalysis of platinum to give the bis hydrochloride monohydrate of 2,4-diamino-5-{3'-[2''-hydroxy-3''-(p-aminophenoxy)propoxy]-4'-methoxybenzyl}pyrimidine.

Anal. Calcd for $C_{21}H_{25}N_5O_4.HCl.H_2O$: C, 50.21; H, 5.81; N, 13.94. Found: C, 50134; H, 6.02; N, 13.51.

Employing substantially the same procedure of Example 7, but substituting for the 2,4-diamino-5-{3'-[2''-hydroxy-3''-(p-nitrophenoxy)propoxy]-4'-methoxybenzyl}pyrimidine used therein an equimolar amount of one of the following nitro compounds:

(1) 2,4-diamino-5-{3'-[3''-(p-nitrophenoxy)propoxy]-4'-methoxybenzyl}pyrimidine
(2) 2,4-Diamino-5-{3'-methoxy-4'-[3''-(p-nitrophenoxy)propoxy]benzyl}pyrimidine
(3) 2,4-Diamino-5-{4'-methoxy-3'-[2''-(p-nitrobenzenesulfonamido]ethoxybenzyl}pyrimidine
(4) 2,4-Diamino-5-{3'-[2''-hydroxy-3''-(p-nitrophenoxy)propoxy]-4',5'-dimethoxybenzyl}pyrimidine
(5) 2,4-Diamino-5-{4'-[2''-hydroxy-3''-(p-nitrophenoxy)propoxy]-3',5'-dimethoxybenzyl}pyrimidine
(6) 2,4-Diamino-5-{3'-[2''-hydroxy-3''-(p-nitrophenoxy)propoxy]-4'-ethoxy-5'-methoxybenzyl}pyrimidine there are produced the following corresponding reduced derivatives:

(1) 2,4-Diamino-5-{3'-[3''-(p-aminophenoxy)propoxy]4'-methoxybenzyl}pyrimidine
(2) 2,4-Diamino-5-{4'-[3''-(p-aminophenoxy)propoxy]3'-methoxybenzyl}pyrimidine
(3) 2,4-Diamino-5-{3'-[2''-(p-aminobenzenesulfonamido)ethoxy]-4-methoxybenzyl}pyrimidine
(4) 2,4-Diamino-5-{3'-[2''-hydroxy-3''-(p-aminophenoxy)propoxy]-4',5'-dimethoxybenzyl}pyrimidine
(5) 2,4-Diamino-5-{4'-[2''-hydroxy-3''-(p-aminophenoxy)propoxy]-3',5'-dimethoxybenzyl}pyrimidine
(6) 2,4-Diamino-5-{3'-[2''-hydroxy-3''-(p-aminophenoxy)propoxy]-4'-ethoxy-5'-methoxybenzyl}pyrimidine.

EXAMPLE 8

2,4-Diamino-5-[4'-methoxy-3'-(3''-benzoylpropoxy)benzyl]pyrimidine

Step A: Preparation of 2-phenyl-2-(3'-chloropropyl)dioxolane

A mixture of 36.5 g (0.2 mole) of γ-chlorobutyrophenone, 14 g of ethylene glycol (0.25 mole), 125 ml of toluene, and 0.1 g of p-toluenesulfonic acid is refluxed under a Dean-Stark trap for 1 hr. An additional 4 g of ethylene glycol is added and reflux continued for 3 hrs more. After cooling, the reaction mixture is washed with 5% sodium bicarbonate solution, dried with anhydrous magnesium sulfate, and concentrated. Upon standing at −10° C. overnight, the mixture partially crystallizes. The crystalline product is filtered and washed with petroleum ether to afford 17.7 g of 2-phenyl-2-(3'-chloropropyl)dioxolane, m.p. 56°–58°.

Step B: Preparation of Ethylene Ketal of 2,4-Diamino-5-[4'-methoxy-3'-(3''-benzoylpropoxybenzyl]pyrimidine A mixture of 1.42 g. of 2,4-diamino-5-(3'-hydroxy-4'-methoxybenzyl)pyrimidine hydrochloride is heated at reflux with 1.2 g. of 2-phenyl-2-(3'-chloropropyl) dioxolane in 30 ml of methanol and 5 ml of an aqueous solution containing 0.6 g. of potassium hydroxide to afford the ethylene ketal of 2,4-diamino-5-[3'-(3''-benzoylpropoxy)-4'-methoxy-benzyl]pyrimidine.

Anal. Calcd for $C_{24}H_{28}N_4O_4$: C, 66.03; H, 6.47; N, 12.84 Found: C, 65.94; H, 6.48; N, 12.51.

Step C: Preparation of 2,4-Diamino-5-[3'-(3''-benzoylpropoxy)-4'-methoxybenzyl]pyrimidine The ethylene ketal of the title compound (0.5 g) is heated at reflux for 1.5 hr. in a mixture of 7.5 ml ethanol, 4.5 ml of water, and 0.75 ml of conc. HCl. The resulting solution is mixed with 25 ml of 2 N sodium hydroxide and refrigerated. The solid product is collected (0.41 g). A sample is recrystallized from ethanol to give pure 2,4-diamino-5-[3'-(3''-benzoylpropoxy)-4'-methoxybenzyl]pyrimidine.

Employing the procedure substantially as described in Example 8, but substituting for 2,4-diamino-5-(3'-hydroxy-4'-methoxybenzyl)pyrimidine hydrochloride used therein, an equimolar amount of 2,4-diamino-5-(4'- hydroxy-3'-methoxybenzyl)pyrimidine hydrochloride, there is produced 2,4-diamino-5-[4'-(3''-benzoylpropoxy)-3'-methoxybenzyl]pyrimidine.

EXAMPLE 9

2,4-Diamino-5-{3'-[3''-(p-acetamidophenylsulfinyl)propoxy]-4-methoxybenzyl}pyrimidine Step A: Preparation of 3-(p-acetamidophenylsulfinyl)propylchloride A solution of 1.22 g (0.005 mole) of 3-(p-acetamidophenylthio)propyl chloride in 25 ml of methylene chloride is cooled in an ice bath while 0.88 g (0.005 mole) of m-chloroperbenzoic acid is added in portions. After keeping at room temperature overnight the reaction mixture is washed with excess 0.5 N sodium hydroxide, dried, and concentrated to a light brown oil. By triturating with ether, 1.06 g of 3-(p-acetamidophenylsulfinyl)propyl chloride are obtained. Anal. Calcd for $C_{11}H_{14}ClNO_2S$: C, 50.86; H, 5.45; N, 5.39; Cl, 13.65. Found: C, 50.53; H, 5.59; N, 5.23; Cl, 13.67.

Step B: Preparation of 2,4-Diamino-5-{3'-[3''-(p-acetamidophenylsulfinyl)propoxy]-4-methoxybenzyl}pyrimidine Following substantially the procedure of Example 1, Step E, 2,4-diamino-5-(3'-hydroxy-4'-methoxybenzyl)-pyrimidine hydrochloride is treated with 3-(p-acetamidophenylsulfinyl)propyl chloride to afford 2,4-diamino-5-3'-[3''-(p-acetamidophenylsulfinyl)propoxy]-4-methoxybenzyl pyrimidine. Nmr, ir and mass spectra are in accord with the structure.

EXAMPLE 10

2,4-Diamino-5-{3'-[3''-(p-acetamidophenylsulfinyl)propoxy]-4-methoxybenzyl}pyrimidine Step A: Preparation of 3-(p-acetamidophenylsulfinyl)propyl chloride A solution of 1.22 g. (0.005 mole) of 3-(p-acetamidophenylthio)propyl chloride in 25 ml. of methylene chloride is cooled in an ice bath while 0.88 g. (0.005 mole) of m-chloro-perbenzoic acid is added in portions. After keeping at room temperature overnight the reaction mixture is washed with excess 0.5 N sodium hydroxide, dried, and concentrated to a light brown oil. By triturating with ether, 1.06 g. of 3-(p-acetamidophenylsulfinyl)propyl chloride is obtained. Anal. Calcd for $C_{11}H_{14}ClNO_2S$: C, 50.86; H, 5.43; N, 5.39; Cl, 13.65. Found: C, 50.53; H, 5.59; N, 5.23; Cl, 13.67.

Step B: Preparation of 2,4-Diamino-5-{3'-[3''-p-acetamidophenylsulfinyl)propoxy]-4-methoxybenzyl}pyrimidine Following substantially the procedure of Example 1, Step B, 2,4-diamino-5-(3'-hydroxy-4'-methoxybenzyl)-pyrimidine hydrochloride is treated with 3-(p-acetamidophenylsulfinyl)propyl chloride to afford 2,4-diamino-5-3'-[3''-(p-acetamidophenylsulfinyl)propoxy]-4-methoxybenzyl pyrimidine. Nmr, ir and mass spectra are in accord with the structure.

Employing the procedure substantially as described in Example 11, but substituting for 3-(p-acetamidophenylsulfinyl)propyl chloride used therein an equimolar amount of 2-(p-acetamidophenylsulfinyl)ethylchloride, there is produced 2,4-diamino-5-{3'-[2''-(p-acetamidophenylsulfinylethoxy]-4-methoxybenzyl}-pyrimidine.

EXAMPLE 11

2,4-Diamino-5-{3'-[3''-(p-acetamidophenylsulfonyl)propoxy]-4-methoxybenzyl}pyrimidine Step A: Preparation of 3-(p-acetamidophenylsulfonyl)propyl chloride A mixture of 1.22 g. of 3-(p-acetamidophenylthio)-propyl chloride in 50 ml. of benzene is warmed on the steam bath until all of the solid is dissolved. To the warm solution is added 2.58 g. of m-chloroperbenzoic acid in portions. A vigorous exothermic reaction occurs. The mixture is heated on the steam bath for a few minutes and then kept at room temperature overnight. The resulting suspension of crystalline product is stirred vigorously with 0.1 N NaOH, filtered, and washed with water and with benzene to give 1.29 g. of 3-(p-acetamidophenylsulfonyl)propyl chloride. Anal. Calcd for $C_{11}H_{14}ClNO_3S$: C, 47.91; H, 5.12; N, 5.08; Cl, 12.86. Found: C, 47.89; H, 5.27; N, 4.91; Cl, 12.70.

Step B: Preparation of 2,4-Diamino-5-{3'-[3''-(p-acetamidophenylsulfonyl)propoxy]-4-methoxybenzyl}pyrimidine Following substantially the procedure of Example 1, Step B, 2,4-diamino-5-(3'-hydroxy-4'-methoxybenzyl)-pyrimidine hydrochloride is treated with 3-(p-acetamidophenylsulfonyl)propyl chloride to afford 2,4-diamino-5-{3'-[3''-(p-acetamidophenylsulfonyl)propoxy]-4-methoxybenzyl}pyrimidine in 80% yield.

Anal. Calcd for $C_{23}H_{27}N_5O_5S.H_2O$: C, 54.86; H, 5.81; N, 13.91; Found: C, 55.17; H, 5.75; N, 13.58.

Employing the procedure substantially as described in Example 12, Steps A and B but substituting for 3-(p-acetamidophenylthio)propyl chloride used therein, an equimolar amount of 2-(p-acetamidophenylthio)ethyl chloride, there is produced 2,4-diamino-5-{3'-[2'-(p-acetamidophenylsulfonyl)ethoxy]-4-methoxybenzyl}-pyrimidine.

EXAMPLE 12

2,4-Diamino-5-{3'-[3''-(p-aminophenylsulfonyl)propoxy]-4-methoxybenzyl}-pyrimidine hydrochloride monohydrate 2,4-Diamino-5-{3''-[p-acetamidophenylsulfonyl)propoxy]-4-methoxybenzyl}pyrimidine (100 mg.) is heated at 95° C. with 1 ml. of 6 N HCl for 1 hour to give crude 2,4-diamino-5-{3'-[3''-(p-aminophenylsulfonyl)propoxy]-4-methoxybenzyl{pyrimidine hydrochloride. After recrystallization from water, the purified product exists as a monohydrate.

Anal. Calcd for $C_{21}H_{25}N_5O_4S.HCl.H_2O$: C, 50.63; H, 5.66; N, 14.05; Cl, 7.12. Found: C, 50,67; H, 5.78; N, 14.21; Cl, 7.43.

EXAMPLE 13

| Preparation of Capsule Formulation | |
| --- | --- |
| Ingredient | Milligrams per Capsule |
| 2,4-Diamino-5-[3'-(3''-benzoylpropoxy)-4'-methoxybenzyl]pyrimidine | 100 |
| Starch | 88 |
| Magnesium sterate | 7 |
| Total Weight: | 195 mg. |

EXAMPLE 14

The active ingredient, starch and magnesium sterate are blended together. The mixture is used to fill hard shell capsules of a suitable size at a fill weight of 100 mg. per capsule.

Preparation of Tablet Formulation

| Ingredient | Milligrams per Tablet |
|---|---|
| 2,4-Diamino-5-{3'-[2"-(p-sulfanilamido)ethoxy]-4'-methoxybenzyl}pyrimidine | 60 |
| Lactose | 200 |
| corn starch (for mix) | 50 |
| Magnesium sterate | 6 |

The active ingredient, lactose and corn starch (for mix) are blended together. The corn starch (for paste) is suspended in water at a ratio of 10 grams of corn starch per 80 milliliters of water and heated with stirring to form a paste. This paste is then used to granulate the mixed powders. The wet granules are passed through a No. 8 screen and dried at about 50° C. The dry granules are passed through a No. 16 screen. The mixture is lubricated with magnesium sterate and compressed into tablets in a suitable tableting machine. Each tablet contains 60 milligrams of active ingredient.

What is claimed is:

1. A compound of the structural formula:

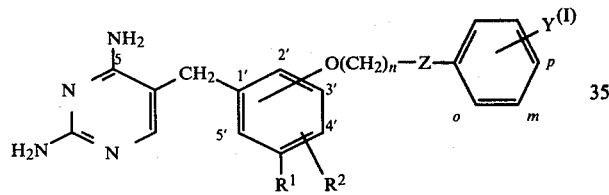

Or pharmaceutically acceptable salt thereof, wherein:

(a)

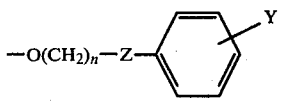

and $R^2$ are independently at position 3' or 4';

(b) Z is oxy, imino, carbonyl, carbamoyl, thio, sulfinyl, sulfonyl or sulfamoyl;

(c) Y is at position o, p, or m and is hydrogen, amino, $C_{1-3}$ alkylamino, $C_{1-3}$ alkanamido, N-$C_{1-3}$ alkylcarbamoyl, nitro or cyano;

(d) n is an integer ranging from 1 to 4; and (e) $R^1$ and $R^2$ are independently hydrogen or $C_{1-5}$ alkoxy.

2. The compound of claim 1 wherein:

(a)

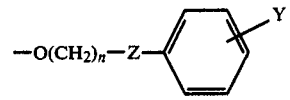

is at position 3';

(b) Z is oxy, carbonyl, sulfamoyl, thio or sulfonyl;

(c) Y is at p-position and is hydrogen, amino, $C_{1-3}$ alkanamido or nitro;

(d) n is an integer ranging from 2 to 3; and (e) $R^1$ and $R^2$ are independently hydrogen or $C_{1-3}$ alkoxy.

3. The compound of claim 1 wherein:

(a)

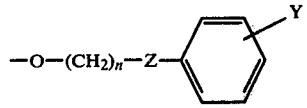

is at position 3';

(b) Z is oxy, carbonyl or sulfamoyl;

(c) Y is at p-position and is hydrogen, amino or acetamido;

(d) n is an integer ranging from 2 to 3; and (e) $R^1$ and $R^2$ are independently hydrogen or methoxy.

4. The compound of claim 1 wherein the compound is:

2,4-diamino-5-{3'-[2"'-(p-sulfanilamido)ethoxy]-4'-methoxybenzyl}pyrimidine;

2,4-diamino-5-{3'-[3"-(p-sulfanilamido)propoxy]-4'-methoxybenzyl}pyrimidine;

2,4-diamino-5-[3'-(3"-benzoylpropoxy)-4'-methoxybenzyl]pyrimidine; or 2,4-diamino-5-[3'-(2"-phenoxyethoxy)-4'-methoxybenzyl]pyrimidine.

5. A method of treating bacterial infections, protozoal diseases and cancer comprising the administration to a mammalian species in need of such treatment an effective amount of a compound according to claim 1.

6. A pharmaceutical composition for treating bacterial infections, protozoal diseases and cancer in a mammalian species comprising a pharmaceutical carrier and an effective amount of a compound according to claim 1.

* * * * *